United States Patent
Amurthur et al.

(10) Patent No.: US 7,664,548 B2
(45) Date of Patent: Feb. 16, 2010

(54) DISTRIBUTED NEUROMODULATION SYSTEM FOR TREATMENT OF CARDIOVASCULAR DISEASE

(75) Inventors: Badri Amurthur, Edina, MN (US); Steven D. Girouard, Chagrin Falls, OH (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 272 days.

(21) Appl. No.: 11/539,301

(22) Filed: Oct. 6, 2006

(65) Prior Publication Data

US 2008/0086185 A1 Apr. 10, 2008

(51) Int. Cl.
*A61N 1/362* (2006.01)
(52) U.S. Cl. ......................................................... 607/9
(58) Field of Classification Search .................. 607/9, 607/46, 62
See application file for complete search history.

(56) References Cited

U.S. PATENT DOCUMENTS

| | | | |
|---|---|---|---|
| 6,141,588 A | 10/2000 | Cox et al. | |
| 7,123,961 B1 | 10/2006 | Kroll et al. | |
| 7,198,603 B2 * | 4/2007 | Penner et al. | 600/486 |
| 7,260,431 B2 | 8/2007 | Libbus et al. | |
| 7,277,761 B2 | 10/2007 | Shelchuk | |
| 2003/0139783 A1 | 7/2003 | Kilgore et al. | |
| 2005/0261741 A1 | 11/2005 | Libbus et al. | |
| 2006/0031378 A1 | 2/2006 | Vallapureddy et al. | |
| 2006/0149337 A1 * | 7/2006 | John | 607/45 |

OTHER PUBLICATIONS

"Biontech—The Bion™ Technology Partnership", [online]. [archived Dec. 14, 2003]. Retrieved from the Internet: <URL: http://web.archive.org/web/20031214070040/www.biontech.org>, (2003), 4 pgs.
PCT Application No. PCT/US2007/070183, International Search Report mailed Nov. 30, 2007, 5 pgs.
PCT Application No. PCT/US2007/070183, Written Opinion mailed Nov. 30, 2007, 7 pgs.
Knott, E. M., et al., "Increased Lymphatic Flow in the Thoracic Duct During Manipulative Intervention", *J Am Osteopath Assoc.*, 105(10), (2005), 447-456.

\* cited by examiner

*Primary Examiner*—George R Evanisko
(74) *Attorney, Agent, or Firm*—Schwegman, Lundberg, Woessner, P.A.

(57) ABSTRACT

A distributed system is described that employs electrical neural stimulation to modulate autonomic activity and which allows titration of the neural stimulation therapy in accordance with physiological measurements reflective of autonomic activity and/or physiological variables affected by the neural stimulation. Such a system may include a plurality of implantable neuromodulation units that communicate with one another over a network.

20 Claims, 4 Drawing Sheets

DISTRIBUTED NEUROMODULATION SYSTEM FOR TREATMENT OF CARDIOVASCULAR DISEASE

FIELD OF THE INVENTION

This patent application pertains to methods and apparatus for the treatment of disease with electro-stimulatory therapy.

BACKGROUND

Heart failure (HF) refers to a clinical syndrome in which an abnormality of cardiac function causes a below normal cardiac output that can fall below a level adequate to meet the metabolic demand of peripheral tissues. It can be due to a variety of etiologies with ischemic heart disease being the most common. When heart failure occurs acutely, such as from a myocardial infarction (MI), autonomic circulatory reflexes are activated that both increase the contractility of the heart and constrict the vasculature as the body tries to defend against the drop in blood pressure. Venous constriction, along with the reduction in the heart's ability to pump blood out of the venous and pulmonary systems (so-called backward failure), causes an increase in the diastolic filling pressure of the ventricles. This increase in preload (i.e., the degree to which the ventricles are stretched by the volume of blood in the ventricles at the end of diastole) causes an increase in stroke volume during systole, a phenomena known as the Frank-Starling principle. If the heart failure is not too severe, this compensation is enough to sustain the patient at a reduced activity level. When moderate heart failure persists, other compensatory mechanisms come into play that characterize the chronic stage of heart failure. The most important of these is the depressing effect of a low cardiac output on renal function due to decreased renal perfusion. The increased fluid retention by the kidneys then results in an increased blood volume and further increased venous return to the heart. A state of compensated heart failure results when the factors that cause increased diastolic filling pressure are able to maintain cardiac output at a normal level even while the pumping ability of the heart is compromised.

Compensated heart failure, however, is a precarious state. If cardiac function worsens or increased cardiac output is required due to increased activity or illness, the compensation may not be able to maintain cardiac output at a level sufficient to maintain normal renal function. Fluid then continues to be retained, causing the progressive peripheral and pulmonary edema that characterizes overt congestive heart failure. Diastolic filling pressure becomes further elevated which causes the heart to become so dilated and edematous that its pumping function deteriorates even more. This condition, in which the heart failure continues to worsen, is decompensated heart failure. It can be detected clinically, principally from the resulting pulmonary congestion and dyspnea, and can lead to rapid death unless appropriate therapy is instituted.

If heart failure persists, a complex remodeling process of the ventricles occurs that involves structural, biochemical, neurohormonal, and electrophysiologic factors. When the ventricles are stretched due to the increased preload over a period of time, the ventricles become dilated. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The increased sympathetic activity increases both the heart's afterload and preload by arterial and vasoconstriction, respectively. Increased sympathetic activity may also depress renal function still further via the renal nerve which causes increased fluid retention and adds to the heart's preload. The sustained stresses caused by the increased loading induce apoptosis (i.e., programmed cell death) of cardiac muscle cells and eventual wall thinning which causes further deterioration in cardiac function. It has been shown that the extent of ventricular remodeling is positively correlated with increased mortality in post-MI and heart failure patients.

Ventricular remodeling in post-MI and HF patients is partly a function of an autonomic imbalance where there is in an increased level of sympathetic activity relative to parasympathetic activity. A similar autonomic imbalance exits in patients suffering hypertension and may be a factor in the development and progression of the disease. Long-standing hypertension is a common cause of heart failure.

DETAILED DESCRIPTION

Figure 1:
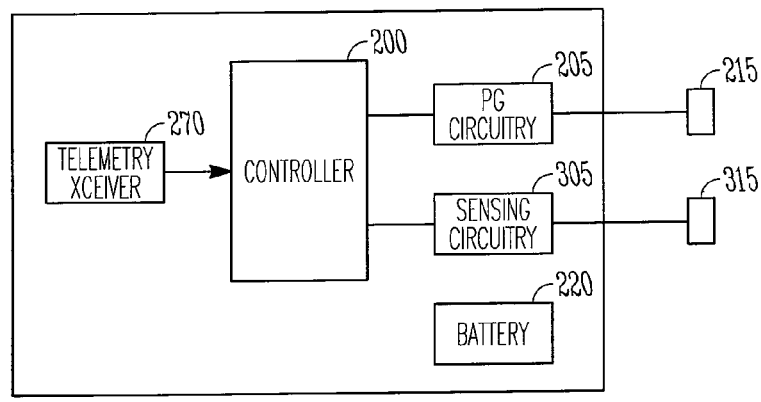
FIG. 1 is a block diagram of an exemplary neuromodulation unit.

As noted above, maladaptive activity of the autonomic nervous system is at least partly responsible for the ventricular remodeling which occurs as a consequence of an MI or heart failure due to other causes and may also contribute to hypertensive disease. All of these conditions can be treated by pharmacological intervention with the use of, for example, ACE inhibitors and beta-blockers. Pharmacological treatment carries with it the risk of side effects, however, and it is also difficult to modulate the effects of drugs in a precise manner.

Described herein are methods and systems that employ electrical neural stimulation to modulate autonomic activity and which allow titration of the neural stimulation therapy in accordance with physiological measurements reflective of autonomic activity and/or physiological variables affected by the neural stimulation. Such methods and systems may be used to treat, for example, chronic heart failure, acute decompensated heart failure, acute MI, hypertension, and renal dysfunction.

As described in greater detail below, neuromodulation therapy may be delivered by a distributed system. Such a system may include a plurality of implantable neuromodulation units wherein each such unit includes a programmable controller, at least one of a neural stimulator and a sensor for sensing a physiological variable affected by neural stimulation, and a telemetry transceiver for communicating over a communication channel. The neuromodulation units are programmed to communicate with one another via telemetry as network nodes to form a network of neuromodulation units.

The neuromodulation units are able to exchange information with one another and deliver neuromodulation therapy in a coordinated manner. The delivery of neural stimulation by a particular unit may be controlled in a closed-loop fashion in accordance with one or more physiological variables measured by that particular unit or other units. Delivering neuromodulation therapy with a distributed system enables the system to be easily reconfigured should the patient's needs change or particular units fail. The neuromodulation units may be programmed such that the network is automatically reconfigured when one or more neuromodulation units are taken in or out of service.

In order to treat cardiac remodeling, renal dysfunction, and/or hypertensive disease, the neural stimulation delivered by the distributed system is applied to one or more selected neural sites via appropriately positioned electrodes in a manner that results in parasympathetic stimulation and/or sympathetic inhibition. Such neural stimulation may be delivered directly to an efferent parasympathetic nerve such as the vagus nerve or to an afferent nerve such as a baroreceptor that causes parasympathetic stimulation and/or sympathetic inhibition via a reflex arc. The vagus nerve provides parasympathetic stimulation to the heart which counteracts the effects of increased sympathetic activity, and stimulation of the vagus nerve at either a pre-ganglionic or post-ganglionic site produces dilation of the coronary arteries and a reduced workload on the heart. Vagal stimulation may be delivered, for example, using an intravascular electrode disposed near the vagus (e.g., in the internal jugular vein) or using a nerve cuff electrode (e.g., placed around the cervical vagus nerve bundle). Baroreceptors are sensory nerve endings located in the heart and vasculature that are stimulated by increased fluid pressure. Stimulation of baroreceptors causes impulses to be relayed via afferent pathways to nuclei in the brainstem that result in parasympathetic activation and sympathetic inhibition. Baroreflex stimulation may be brought about using a nerve cuff electrode placed around the aortic or carotid sinus nerve or using an intravascular electrode disposed near baroreceptors in the heart or pulmonary artery. Neural stimulation could similarly be delivered to other sympathetic/parasympathetic targets such as chemoreceptors and nerves innervating organs such as the kidney. The distributed system for delivering neuromodulation therapy may also include a cardiac resynchronization device, defibrillator and/or pacemaker.

Exemplary Neuromodulation Unit

FIG. 1 is a system diagram of the electronic components of an exemplary neuromodulation unit. The components may be contained within an implantable housing that may be implanted at an appropriate location in order to perform its stimulation and/or sensing function. A neuromodulation unit may also be an external device. In the illustrated embodiment, a programmable electronic controller 200 is interfaced to pulse generation circuitry 205 for controlling the output of neural stimulation pulses and interfaced to sensing circuitry 305 for sensing physiological variables. The controller is also interfaced to an RF telemetry transceiver 270 that enables the unit's networking functions. A battery 220 also contained within the housing provides power to the device. In one embodiment, the battery is rechargeable and may be recharged transcutaneously. The controller 200 may be made up of a microprocessor communicating with a memory, where the memory may comprise a ROM (read-only memory) for program storage and a RAM (random-access memory) for data storage. The controller could also be implemented by other types of logic circuitry (e.g., discrete components or programmable logic arrays) using a state machine type of design. As the term is used herein, the programming of the controller refers to either code executed by a microprocessor or to specific configurations of hardware components for performing particular functions. The controller includes circuitry for generating clock signals used to keep track of lapsed time intervals and deliver neural stimulation in accordance with a defined duty cycle or schedule. The pulse generation circuitry 205 may be similar to that used in cardiac pacemakers and delivers electrical stimulation pulses to one or more neural stimulation electrodes 215. The electrodes may be bipolar or unipolar and may be integral to the unit housing or connected to the pulse generation circuitry by a lead that may be implanted, for example, subcutaneously or intravascularly. The pulse frequency, pulse width, pulse amplitude, pulse polarity, burst duration, and bipolar/unipolar stimulation configuration in this embodiment are programmable parameters, the optimal settings of which depend upon the stimulation site and type of stimulation electrode. The sensing circuitry 305 is connected to one or more electrodes 315 or other types of transducers for sensing physiological variables affected by neural stimulation and/or reflective of autonomic balance. The unit may then be programmed to use these variables as well as variables sensed by other units in the network for controlling the delivery of neural stimulation. In various embodiments, the sensing circuitry 305 and electrode 315 or other transducer may be a sensing channel for detecting cardiac electrical activity, a minute ventilation sensor, an accelerometer, a transthoracic impedance sensor, a chemosensor, or a pressure sensor. Examples of physiological variables that could be measured using these various sensing modalities include heart rate, heart rate variability, respiratory rate, activity level, blood oxygen concentration, blood electrolyte concentration, cardiac output, and blood pressure.

Combination Cardiac Device/Neuromodulation Unit

A neuromodulation unit may also be incorporated into an implantable cardiac device such a pacemaker or implantable cardioverter/defibrillator. Implantable cardiac devices have been developed that provide appropriately timed electrical stimulation to one or more heart chambers in an attempt to improve the coordination of atrial and/or ventricular contractions in heart failure patients, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace. A neuromodulation unit such as described above may also be incorporated into an implantable cardiac device configured to deliver conventional bradycardia pacing, anti-tachyarrhythmia therapy, and/or CRT. It has also been found that CRT can be beneficial in reducing the deleterious ventricular remodeling which can occur in post-MI and heart failure patients as a result of changes in the distribution of wall stress experienced by the ventricles during the cardiac pumping cycle when CRT is applied to pre-excite particular areas of the ventricles. By pacing one or more sites in a ventricle, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Figure 2:
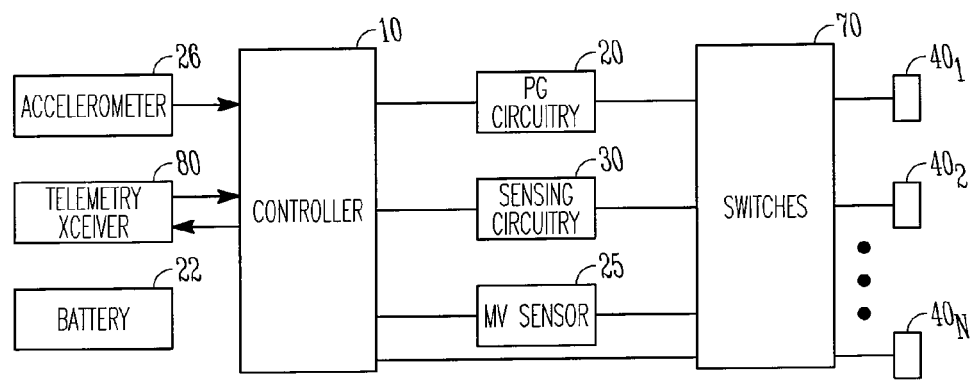
FIG. 2 is a block diagram of a neuromodulation unit incorporated into an implantable cardiac device.

FIG. 2 illustrates an embodiment of a neuromodulation unit that is incorporated into an implantable cardiac rhythm management device which has cardiac pacing and/or cardioversion/defibrillation functionality. The device is battery-powered and equipped with multiple sensing and pacing channels which may be physically configured to sense and/or pace the atria or the ventricles in a variety of pacing modes including conventional bradycardia pacing and cardiac resynchronization pacing. A battery 22 supplies power to the circuitry. The controller 10 controls the overall operation of the device in accordance with programmed instructions and/or circuit configurations and includes timing circuitry such as external clocks for implementing timers used to measure lapsed intervals and schedule events. Interfaced to the controller are sensing circuitry 30 and pulse generation circuitry 20 by which the controller interprets sensing signals and controls the delivery of paces in accordance with a pacing mode. An exertion level sensor (such as the accelerometer 26 or the minute ventilation sensor 25 shown in FIG. 2 or other sensor that measures a parameter related to metabolic demand) enables the controller to adapt the pacing rate in accordance with changes in the patient's physical activity. A telemetry transceiver 80 is interfaced to the controller that enables the device to communicate with other neuromodulation units in the network as well as communicate with an external device such as an external programmer and/or a remote monitoring unit.

The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge or current source pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. The pulse generation circuitry may also include a shocking pulse generator for delivering a defibrillation/cardioversion shock via a shock electrode upon detection of a tachyarrhythmia.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. One or more pacing channels may also be configured, by appropriate lead placement and pulse energy/frequency settings, for delivering electrical stimulation to stimulate sympathetic and/or parasympathetic nerves. For example, a lead with a stimulation electrode may be placed in proximity to the vagus nerve in order to stimulate that nerve and increase parasympathetic activity. The pulse generator for the neural stimulation channel outputs a train of neural stimulation pulses that may be varied by the controller as to amplitude, frequency, pulse width, and burst duration.

Pulse Generation Circuitry

Figure 3:
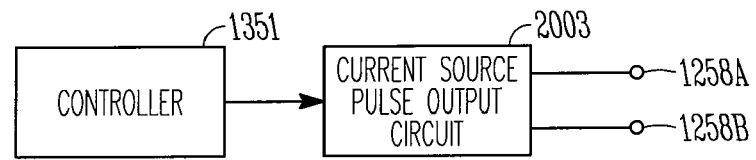
FIGS. 3 and 4 illustrate different embodiments of circuitry for delivering neural stimulation pulse trains.
Figure 4:
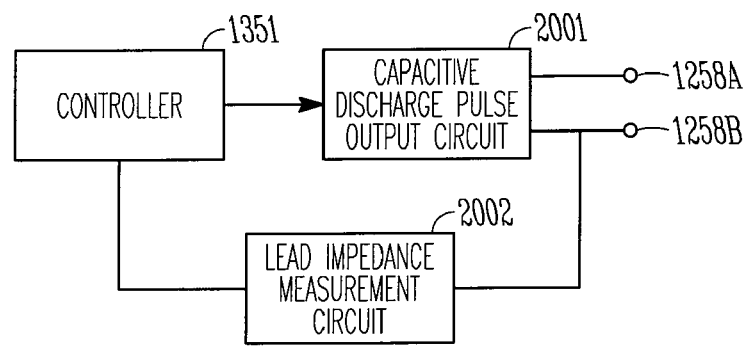

FIGS. 3 and 4 illustrate different embodiments of circuitry for delivering neural stimulation pulse trains as described above such as the pulse generators in FIG. 1 and FIG. 2. In FIG. 3, a current source pulse output circuit 2003 outputs current pulses between stimulation electrodes 1258A and 1258B in accordance with command inputs from the controller 1351. The command inputs from the controller which may be programmed by a user, as well as adjusted in accordance with measured physiological variables, specify the frequency of the pulses, pulse widths, current amplitude, pulse polarity, and whether unipolar or bipolar stimulation is to be delivered. FIG. 4 illustrates another embodiment in which a capacitive discharge pulse output circuit 2001 is used to output voltage pulses between stimulation electrodes 1258A and 1258B in accordance with command inputs from the controller 1351. In this embodiment, the command inputs from the controller which may be programmed by a user specify the frequency of the pulses, pulse widths, voltage amplitude, pulse polarity, and whether unipolar or bipolar stimulation is to be delivered. In order for the controller to specify a voltage amplitude that results in a desired current amplitude for the pulses, the lead impedance may be measured by lead impedance measurement circuit 2002. The output capacitor of the pulse output circuit may then be charged to the appropriate voltage for each pulse. In order to monitor the lead impedance, the controller is programmed to periodically, or upon command from a user via telemetry, charge the output capacitor to a known voltage level, connect the output capacitor to the stimulation leads to deliver a stimulation pulse, and measure the time it takes for the capacitor voltage to decay by a certain amount (e.g., to half of the initial value). In order to minimize patient discomfort, the lead impedance procedure should be performed using as low a voltage as possible. In one embodiment, the controller is programmed to use a first voltage amplitude (e.g., 1 volt) and then compare the measurement count (i.e., the capacitor decay time) to a specified minimum value CntZMin. If the measurement count is below CntZMin, the current delivered during the test is deemed too small for the measurement to be accurate. A second measurement pulse is then delivered at a higher second voltage (e.g., 2 volts). If that count is again below CntZMin, a third measurement pulse is delivered at a still higher third voltage (e.g., 4 volts). With a typical stimulation lead, this procedure limits the measurement current to between roughly 0.6 mA and 1 mA.

Neuromodulation Network

A plurality of neuromodulation units as described above may be configured to communicate with one another over a telemetry communications channel and form a neuromodulation network in which each neuromodulation unit is a network node. Individual neuromodulation units may be configured with different sensing modalities for measuring a plurality of physiological variables, which measurements may be shared with other units in the network. Neuromodulation units with neural stimulation functionality may be disposed at different anatomical locations to enable different types of stimulation to be delivered in accordance with the shared physiological variable measurements.

The neuromodulation units in one embodiment communicate with one another via RF telemetry. (Other embodiments may employ other types of communications such as acoustic.) The units may form a network according to a master/slave paradigm in which one of the units, such as an implantable cardiac device, serves as a master that communicates with the other units, designated as satellite or slave units. In another embodiment, a peer-to-peer networking scheme is employed. In this network, each neuromodulation unit has the independent capability of communicating bi-directionally with every other neuromodulation unit. The units may exchange sensor data, functional status, etc. with other units. The units operate independently, and a unit does not cease to function if any other unit is absent. The units may be programmed such that the network is automatically reconfigured upon a unit being taken in or out of service. When a unit is removed from the network, the lack of communication from that unit is detected by the other units. Algorithms for controlling the delivery of neural stimulation by the other units that depend upon physiological measurements obtained by the removed unit can then be adjusted appropriately. When a new unit joins the network, the new unit communicates to the other units in the network information as to its stimulation and/or sensing functionality, allowing the other units to adjust their behavior as appropriate (e.g., to make use a newly sensed physiological variable to control neural stimulation). The neuromodulation units may also be programmed to connect in an ad hoc manner so as to self-organize into the network.

Figure 5:
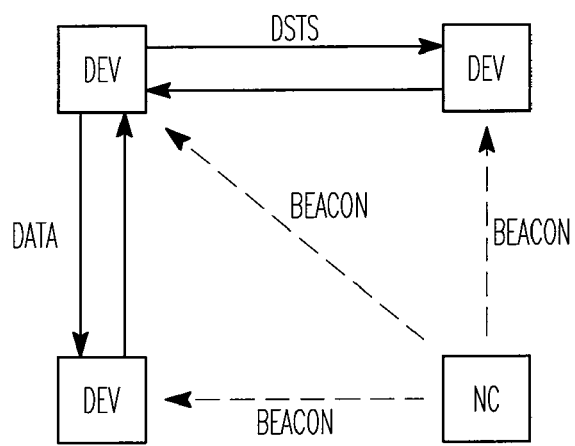
FIG. 5 illustrates an exemplary network.

An exemplary network is illustrated in FIG. 5 which shows a plurality of nodes. The network follows a master/slave paradigm in which the network node serving as the master is designated as the network coordinator (NC), while the remaining nodes in the network are slaves and designated as member nodes or as devices (DEV). All of the nodes which are joined together in the network may communicate with one another over a defined communications channel. The primary function of the NC is to establish the basic timing for the network, which it does by periodically broadcasting beacons which define time allocations for the different devices to transmit data. In other embodiments, beacons may be transmitted by one or more nodes in a distributed manner. As described below, a beacon designates the start of a frame which contains the individual time slots allocated to the devices for transmitting data.

Figure 6:
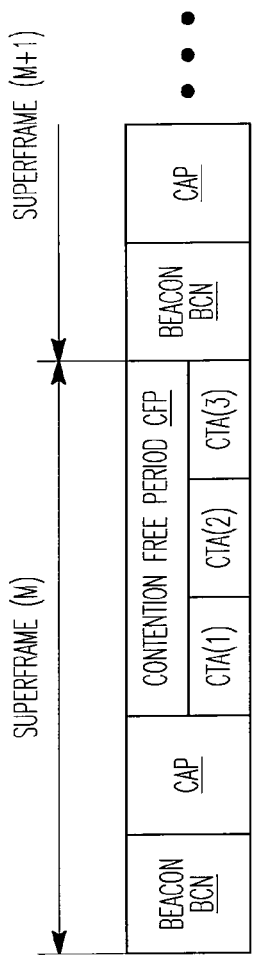
FIG. 6 illustrates a communications frame.

The beacons broadcast by a NC divide time into frames, the typical structure of a frame(m) being shown in FIG. 6. The frame is made up of three main parts. The first part is the beacon which allows devices to synchronize to a network and contains information which identify the network, the frame duration, and the channel time allocations. The beacon (BCN) thus contains descriptions of the time allocations for the entire frame. The second part of the frame is the contention access period (CAP) which can be used for signaling messages as well as small data transfers and access to which is based on CSMA/CA (Carrier Sense Multiple Access with Collision Avoidance). The third part is the contention free access period (CFP) which is accessed by devices in a manner dictated by the PNC based on a TDMA (time division multiple access) mechanism. The CFP is divided into time slots called channel time allocations (CTAs) which are used for data transfer by the member devices of the network.

Exemplary Distributed Neuromodulation Systems

Figure 7:
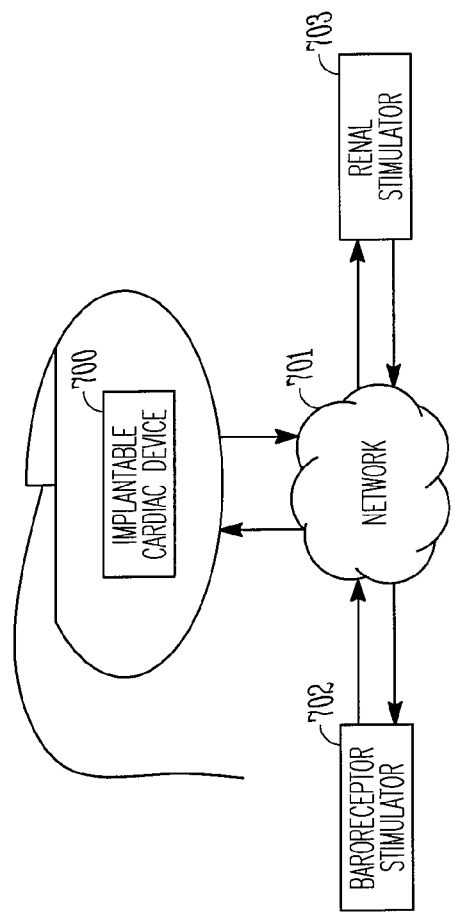
FIG. 7 illustrates an exemplary distributed neuromodulation system.

FIG. 7 illustrates an exemplary distributed neuromodulation system that includes three neuromodulation units. An implantable cardiac device 700 is configured to deliver vagal stimulation as an anti-remodeling therapy for treating HF or MI. The device 700 could also be configured to perform other functions such as bradycardia pacing, tachyarrhythmia detection and treatment, and resynchronization pacing. The device 700 communicates via the network 701 with a renal stimulator 703 that delivers stimulation pulses in a manner that inhibits the renal nerve and improves renal function. The device 700 also communicates via the network 701 with a baroreceptor stimulator 702 for chronic lowering of blood pressure as an anti-hypertensive therapy.

In an exemplary embodiment, each neuromodulation unit with a neural stimulation functionality such as described above is configured to alternate between operating in either a neural stimulating (NS) state or a non-neural stimulating (non-NS) state. When in the NS state, the unit delivers neural stimulation according to programmed stimulation parameters. In the non-NS state, the unit delivers no neural stimulation. The durations of the NS and non-NS states thus define a neural stimulation duty cycle. For example, the unit could be programmed to deliver a burst of neural stimulation pulses in the NS state for 10 seconds and then enter the non-NS state for 50 seconds in which no stimulation pulses are delivered. As described below, the unit may be programmed to deliver neural stimulation in a closed-loop manner by varying the duty cycle of the NS state and/or varying one or more other stimulation parameters in response to one or more sensed physiological variables related to the patient's autonomic balance and/or affected by the neural stimulation. In the embodiments described below, reference is made to a generic physiological variable PV that may represent one of more of the physiological variables discussed herein. Also, the physiological variable PV may be an instantaneous measurement or an average of previously measured values over some specified period of time. The physiological variable PV may also represent measurement of a single variable or a composite function of a plurality of variables. For example, PV may be a weighted average of heart rate, blood pressure, activity level, and respiratory rate.

Figure 8:
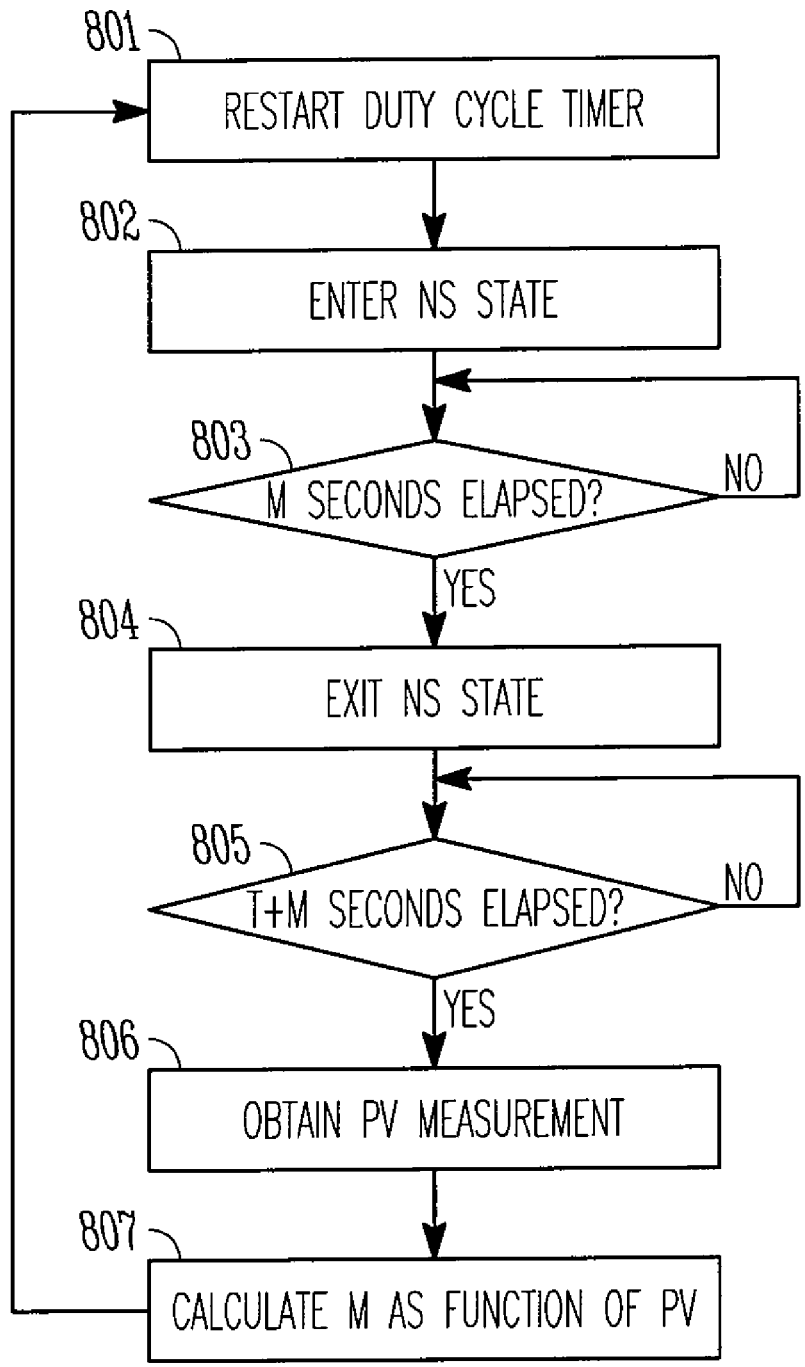
FIG. 8 illustrates an algorithm for adjusting the neural stimulation duty cycle.

A neuromodulation unit may be programmed to adjust the duty cycle of the neural stimulation state in accordance with measurement of one or more physiological variables related to the patient's autonomic balance. For example, the duty cycle for delivering vagal stimulation may be increased upon measurement of a physiological variable that indicates an increased sympathetic tone. The physiological variable measurements may be obtained the unit itself or received from other units over the network. FIG. 8 illustrates an exemplary algorithm that could be executed by the controller to implement such duty cycling. The algorithm begins after the unit has exited the neural stimulation state and is in a non-neural stimulation state where no pre-excitation pacing is being delivered. At step 801, a duty cycle timer is started which counts from zero to T+M seconds (or other unit of time) where T and M are specified values corresponding to the duration of the non-NS and NS states, respectively. At step 802, the unit enters the NS state and begins delivering neural stimulation. At step 803, while continuing to operate in the NS state, the unit monitors the duty cycle timer until M seconds have elapsed, at which point the unit exits the NS state at step 804. The unit then monitors the duty cycle timer at step 805 until T+M seconds have elapsed. The unit then obtains a physiological variable measurement PV at step 806. The value of M is then calculated as a function of the physiological variable measurement PV at step 807. The function for mapping the physiological variable measurement to a value for M could be simple, such as where the value of M alternates between two values according to the value of the physiological variable measurement, or more complicated. In the latter instance, the function could be implemented as a look-up table. Either in addition to or instead of adjusting the duty cycle at step 807, the values of one or more other stimulation parameters could similarly be calculated as functions of the physiological variable measurement. Examples of such stimulation parameters include pulse width, pulse frequency, and pulse amplitude.

As noted earlier, a neuromodulation unit may also be an external device. For example, an external neuromodulation unit with neural stimulation functionality may deliver such neural stimulation transcutaneously by means of electrodes that are positioned to overlie a particular neural stimulation site. The distributed neuromodulation system may also communicate with internal or external components that may or may not be considered neuromodulation units. For example, the distributed neuromodulation system could communicate with an external physiologic monitor, an example of which could be a device that includes a weight scale and blood pressure cuff together with a telemetry transceiver. The distributed neuromodulation system could also communicate with a remote monitoring device. The remote monitoring device may be further interfaced to a network (e.g., an internet connection) for communicating with a patient management server that allows clinical personnel at remote locations to receive data from the remote monitoring device as well as issue commands. The controllers of the neuromodulation units may be programmed such when particular conditions are detected (such as when a measured parameter exceeds or falls below a specified limit value), the unit transmits an alarm message to the remote monitoring device and to the patient management server to alert clinical personnel.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A system for delivering neuromodulation therapy, comprising:
    a plurality of implantable neuromodulation units wherein each such unit includes a programmable controller, at least one of a neural stimulator and a sensor for measuring a physiological variable affected by neural stimulation, and a telemetry transceiver for communicating over a communication channel;
    wherein each of the neuromodulation units are programmed to communicate bidirectionally and exchange functional status with one another via telemetry as network nodes to form a network of neuromodulation units that is able to deliver neuromodulation therapy in a coordinated manner;
    wherein the neuromodulation units are programmed such that the network is automatically reconfigured when one or more neuromodulation units are taken in or out of service;
    wherein the neuromodulation units are programmed such that, when a unit that measures a physiological variable is removed from the network, the other units of the network detect the lack of communication from the removed unit and adjust algorithms for controlling the delivery of neural stimulation that depend upon the physiological measurements obtained by the removed unit; and,
    wherein the neuromodulation units are programmed such that, when a new unit joins the network, the new unit communicates to the other units in the network information as to its stimulation and/or sensing functionality.

2. The system of claim 1 wherein one of the implantable neuromodulation units is an implantable cardiac rhythm management device.

3. The system of claim 1 wherein the neuromodulation units are programmed to connect in an ad hoc manner so as to self-organize into the network.

4. The system of claim 1 wherein the neuromodulation units communicate over the network via time division multiplexing with one particular neuromodulation unit serving as a network coordinator for transmitting beacons that divide time into frames that are further divided into time slots for communications between the units.

5. The system of claim 1 wherein a unit with a sensor for measuring a physiological variable is programmed to transmit the measurement to other units over the network.

6. The system of claim 1 wherein a unit with a neural stimulator is programmed to adjust the amount of neural stimulation delivered in accordance with measurements of one or more physiological variables obtained directly or received over the network.

7. The system of claim 1 wherein a unit with a neural stimulator is programmed to deliver bursts of neural stimulation pulses according to a duty cycle that alternates between a neural stimulation state and a non-neural stimulation state.

8. The system of claim 7 wherein a unit with a neural stimulator is programmed to adjust the durations of the neural stimulation and non-neural stimulation states in accordance with the physiological variable measurement.

9. The system of claim 1 wherein the physiological variable measurement is an average of the signal related to a patient's physiological variable as generated over a specified period of time.

10. The system of claim 1 wherein a unit with a neural stimulator is programmed to adjust the amount of neural stimulation in accordance with a weighted average of a plurality of measured physiological variables received over the network.

11. The system of claim 1 wherein the neuromodulation units are battery powered with a rechargeable battery that may be transcutaneously recharged.

12. The system of claim 1 further comprising one or more external neuromodulation units configured for delivering neural stimulation transcutaneously.

13. The system of claim 1 wherein the plurality of neuromodulation units are further programmed to transmit data and/or receive commands from a patient management server via a network connection.

14. A method for delivering neuromodulation therapy, comprising:
    implanting a plurality of implantable neuromodulation units wherein each such unit includes a programmable controller, at least one of a neural stimulator and a sensor for measuring a physiological variable affected by neural stimulation, and a telemetry transceiver for communicating over a communication channel;
    programming each of the neuromodulation units to communicate bidirectionally and exchange functional status with one another via telemetry as network nodes to form a network of neuromodulation units that is able to deliver neuromodulation therapy in a coordinated manner;
    programming the neuromodulation units such that the network is automatically reconfigured when one or more neuromodulation units are taken in or out of service;
    programming the neuromodulation units such that, when a unit that measures a physiological variable is removed from the network, the other units of the network detect the lack of communication from the removed unit and adjust algorithms for controlling the delivery of neural stimulation that depend upon the physiological measurements obtained by the removed unit; and, programming the neuromodulation units such that, when a new unit joins the network, the new unit communicates to the other units in the network information as to its stimulation and/or sensing functionality.

15. The method of claim 14 wherein one of the implantable neuromodulation units is an implantable cardiac rhythm management device.

16. The method of claim 14 further comprising programming the neuromodulation units to connect in an ad hoc manner so as to self-organize into the network.

17. The method of claim 14 further comprising programming the neuromodulation units to communicate over the network via time division multiplexing with one particular neuromodulation unit serving as a network coordinator for transmitting beacons that divide time into frames that are further divided into time slots for communications between the units.

18. The method of claim 14 further comprising programming a unit with a sensor for measuring a physiological variable to transmit the measurement to other units over the network.

19. The method of claim 14 further comprising programming a unit with a neural stimulator to adjust the amount of neural stimulation delivered in accordance with measurements of one or more physiological variables obtained directly or received over the network.

20. The method of claim 14 further comprising:

programming a unit with a neural stimulator to deliver bursts of neural stimulation pulses according to a duty cycle that alternates between a neural stimulation state and a non-neural stimulation state; and, programming a unit with a neural stimulator to adjust the durations of the neural stimulation and non-neural stimulation states in accordance with the physiological variable measurement.

* * * * *